(12) United States Patent
Cho et al.

(10) Patent No.: US 8,673,331 B2
(45) Date of Patent: Mar. 18, 2014

(54) COMPOSITION WITH STERILIZING ACTIVITY AGAINST BACTERIA, FUNGUS AND VIRUSES, APPLICATION THEREOF AND METHOD FOR PREPARATION THEREOF

(75) Inventors: Il Hoon Cho, Daejeon (KR); Dong Gyu Lee, Daejeon (KR); Young Yeol Yang, Daejeon (KR)

(73) Assignee: GP&E, Daejeon (KR)

( * ) Notice: Subject to any disclaimer, the term of this patent is extended or adjusted under 35 U.S.C. 154(b) by 0 days.

(21) Appl. No.: 13/299,697

(22) Filed: Nov. 18, 2011

(65) Prior Publication Data

US 2013/0129805 A1 May 23, 2013

(51) Int. Cl.
*A01N 25/08* (2006.01)
*A01N 59/16* (2006.01)

(52) U.S. Cl.
USPC .......................... 424/411; 424/443; 525/418

(58) Field of Classification Search
None
See application file for complete search history.

(56) References Cited

U.S. PATENT DOCUMENTS

2009/0149426 A1\* 6/2009 Lee et al. ..................... 514/63

FOREIGN PATENT DOCUMENTS

| JP | 2000-044473 | | 2/2000 |
|---|---|---|---|
| KR | 10-1998-0007982 | | 4/1998 |
| KR | 10-2001-0057595 | | 7/2001 |
| KR | 10-2002-0008375 | | 1/2002 |
| KR | 10-2003-0037050 | | 5/2003 |
| KR | 10-2003-0063961 | | 7/2003 |
| KR | 2005/077887 | * | 8/2005 |
| KR | 10-2010-0025491 | | 3/2010 |

OTHER PUBLICATIONS

Fu et al.,"Anatase TiO2 Nanocomposites for Antimicrobial Coatings"; J. Phys. Chem. B, 2005, 109 (18), pp. 8889-8898, published Mar. 2005 by The American Chemical Society.*
Khan et al., "Silver Nanoparticles: Green Route, Stability and Effect of Aditives", Journal of Biomaterail and Nanotechnology, 2011, 2, 390-399, published Oct. 2011 by Scientific Research.*

\* cited by examiner

*Primary Examiner* — Anoop Singh
*Assistant Examiner* — Yanzhi Zhang
(74) *Attorney, Agent, or Firm* — Drinker Biddle & Reath LLP

(57) ABSTRACT

Disclosed herein are an anti-bacterial, anti-fungal and anti-viral composition with excellent sterilizing power, deodorization and adhesion activity, an application thereof, and a method for preparing the same. The composition with sterilizing activity against bacteria, fungus and virus comprises colloidal silver particles in an amount of from 11 wt % to 15 wt %, titanium dioxide nanoparticles in an amount of from 18 wt % to 25 wt %, a dispersion stabilizer in an amount of from 0.01 wt % to 10 wt %, a binder in an amount of from 0.1 wt % to 4 wt %, and a balance of water in an amount required to form 100 wt %.

9 Claims, No Drawings

COMPOSITION WITH STERILIZING ACTIVITY AGAINST BACTERIA, FUNGUS AND VIRUSES, APPLICATION THEREOF AND METHOD FOR PREPARATION THEREOF

BACKGROUND OF THE INVENTION

1. Field of the Invention

The present invention relates to an anti-bacterial, anti-fungal and anti-viral composition with excellent sterilizing power, deodorization and adhesion activity, an application thereof, and a method for preparing the same. More particularly, the present invention relates to a composition with sterilizing activity against bacteria, fungi and viruses, comprising silver colloid, titanium dioxide nanoparticles, a dispersion stabilizer, a binder and water, an application thereof, and a method for the preparation thereof.

2. Description of the Related Art

Silver has long been known to show anti-bacterial activity. Particularly, silver colloid, that is, silver clusters (10 to 150 nm in size) evenly dispersed throughout an aqueous solvent, are found to have potently sterilizing activity against approximately 650 species of harmful bacteria and fungi. In addition, it has been observed that when colloidal silver particles are applied to the body that they do not kill most beneficial bacteria.

Further, silver colloid solutions are recognized as a natural substance that has been approved for medical use by the FDA. Recently, colloidal silver has been used as a preservative in foods with the official permission of the FDA. Therefore, colloidal silver is regarded as being non-toxic to the body.

As silver colloid solutions are verified to have potently antibacterial activity while being non-toxic to the body, active studies have been performed to develop silver particles having more effective antibacterial activity, colloidal silver agents for killing pathogenic bacteria and treating diseases, and the use thereof in various products including cosmetics, fibers, wallpaper, washing machines, clothes, etc.

When exposed to light of the proper energy, a photocatalyst shows electrically semiconductive properties, generating active oxygen species or hydroxyl (OH) radicals which induce strong redox reactions responsible for antibacterial activity and the degradation of stinking materials. A certain level of energy causes electrons in a semiconductor to be excited from the valence band to the conduction band. While electrons ($e^-$) are excited to the conduction band, holes ($h^+$) are created in the valance band. These electrons and holes perform various reactions including the degradation of harmful materials by means of potent oxidation or reduction.

Titanium dioxide ($TiO_2$) is representative of photocatalytic oxides and finds the broadest applications in the photocatalytic fields thanks to its chemical stability and excellent semiconductor properties. Titanium dioxide can sufficiently perform photocatalytic activity when an energy of 3.0 eV (a bandgap between the valence band and the conduction band, corresponding to light with a wavelength of 380 nm) is applied thereto.

The electrons ($e^-$) and holes ($h^+$) generated upon the exposure of the photocatalyst titanium dioxide to light respectively react with $O_2$ and $H_2O$ in air to produce the two active oxygen species of a superoxide anion ($O_2^-$) and a hydroxy radical (.OH) on the surface of the titanium oxide. Having redox potential, the hydroxyl radical is able to oxidize most materials whereby it is effectively used to purify NOx, volatile organic compounds (VOCs) and various stingy odors, to remove BOD, chromacity, degradation-refractory contaminants and environmental hormones of livestock wastewater, domestic sewage and industrial wastewater, and to kill various pathogens and bacteria such as pathogenic *Escherichia coli, Staphylococcus aureus*, O-157, etc., with an efficiency of 99% or higher.

Titanium dioxide is economically beneficial because its redox reaction can be elicited by fluorescence light as well as solar light and its performance is semi-permanent through the cycle of "settlement on substance→photolysis→regeneration." In addition, titanium dioxide functions as a photocatalyst in various applications, with the concomitant production of non-toxic materials such as water and $CO_2$.

According to the WHO, SARS (Severe Acute Respiratory Syndrome) is caused by the SARS coronavirus, a variant of the coronavirus causing colds in human. A coronavirus is a kind of RNA virus with a high mutation rate. Further, coronaviruses exhibit high recombination frequency because the synthesis of the RNA viral genome is discontinuous due to template switching.

Coronaviruses infect humans, causing mainly respiratory symptoms such as a cold in the nose. Generally, an infection by the coronavirus has not been regarded as a significant problem because there was only a low risk of infection before the outbreak of SARS. However, they often act as fatal pathogens in some animals such as cow, dogs, pigs, birds, etc., and experts had expected that when mutated in livestock such as pigs, chickens, etc., coronaviruses can cause a fatal disease in the human body. SARS spreads by means of infection via aerogenous droplets, e.g., spit droplets from SARS patients or by contagion via materials (e.g., doorknobs, telephones, keyboards, etc.) contacted by SARS patients.

Human influenza (HI), used to refer to epidemic influenza cases which were caused by influenza virus endemic to human populations and are generally generated at the turning of the seasons and in the winter (e.g., from November to March), can spread rapidly due to the severity of its symptoms and its high infectious potential. Human flu-causing viruses can belong to any of three major influenza-causing Orthomyxoviruses—Influenza A virus, Influenza B virus and Influenza C virus, which are single-stranded RNA viruses.

Particularly, the influenza A virus experiences frequent nuclear rearrangement, causing pandemic flu while the influenza C virus is responsible for respiratory diseases that are not serious.

Avian influenza is an influenza caused by viruses adapted to birds such as poultry or wild birds. As a rule, influenza viruses are classified into A, B and C viruses. Of these, the influenza A and B viruses are known to infect the human body, with a pandemic flu being caused only by the influenza A virus.

On the surface of an influenza virus, there are projections consisting of specific hemagglutinin (HA) and neuraminidase (NA). Because there are 16 different hemagglutinins and 9 different neuraminidases, 166 (=16×9) types of influenza viruses can theoretically exist. Of them, three distinct HAs (H1, H2 and H3) and two different NAs (N1 and N2) are found in human infections while avian influenza infections are associated mainly with the H5 or H7 type.

Among them, H5N1 virus is known as a highly pathogenic influenza virus causing flu in bird and poultry populations. Avian influenza spreads from one bird to another via nose drippings, respiratory secretions, and feces. In most cases, feces carry the avian influenza virus to the mouth. Thus, for example, instruments, feedstock, bird cages, clothes, etc., when contaminated with respiratory secretions or feces of birds, are the main mediators of bird flu.

Since the first report on the outbreak thereof in Mexico and the United States in April, 2009, the so-called new flu, caused by influenza A virus subtype H1N1, also known now as the new H1N1 virus, has spread worldwide.

Until seven days after the appearance of symptoms, the patients infected with the new influenza A virus subtype H1N1 can transmit the virus to healthy persons. The transmittable period of time may be longer for children. Above all, it is important to wash the hands in order to prevent infection with the new influenza A virus. It is recommended to wash the hands frequently and to avoid touching the eyes, the nose and the mouth with the hands because the virus may be on door knobs, public telephones, etc.

Inhibitors against coronaviruses and influenza viruses, and silver- or titanium dioxide photocatalyst-induced sterilization have been described previously.

Products with sterilizing activity against coronaviruses are made mostly from extracts of synthetic organic materials or natural materials (see, for example, Korean Patent Laid-Open Publication No. 2003-0063961 and Japanese Patent Laid-Open Publication No. 2000-44473), which are not inorganic solutions.

Colloidal silver or titanium dioxide is used as an inorganic antibacterial agent. There are various applications using such inorganic antibacterial agent, including silver-coated clothes, antibacterial sprayers (Korean Patent Laid-Open Publication No. 2002-0008375), coating agents for air filters, and the like. Products with silver show almost no changes in performance irrespective of environmental conditions whereas products based on the photocatalyst have insufficient performance under low intensity radiation.

Products using both silver and titanium dioxide and preparation methods thereof are disclosed in Korean Patent Laid-Open Publication Nos. 1998-0007982 (Method for Preparing Inorganic Anti-Bacterial Agent), 2001-0057595 (Method for Preparing Silver-Coated Photocatalyst) and 2003-0037050 (Titanium Dioxide Photocatalyst Containing Anti-Bacterial Metallic Ingredient and Preparation Method thereof).

In Korean Patent Laid-Open Publication No. 2003-0037050, antibacterial metals such as silver is formed into a colloid which is then mixed with titanium dioxide and fabricated into crystalline oxides through hydrothermal synthesis. The crystalline oxides are coated using a sol-gel method and microcapsulated to afford photocatalytic material containing antibacterial metal. Korean Patent Laid-Open Publication No. 1998-0007982 contemplates a silver ion-impregnated inorganic antibacterial agent which is prepared by mixing phosphoric acid, silver nitrate, titanium dioxide powder and colloidal silica, and sintering the mixture. Contemplated by Korean Patent Laid-Open Publication No. 2001-0057595 is a method for preparing microparticular photocatalyst in which photocatalytic powder is coated with silver by intermetallic substitution.

The composition and the synthesis method thereof contemplated by the present invention are constitutionally different from the prior art products and synthesis methods using silver and titanium dioxide.

To overcome the problems encountered in the prior art, the present inventors process the two nanoparticles of colloidal silver and titanium dioxide, both of which exhibit anti-bacterial, anti-fungal and anti-viral activity, in such a simple manner that titanium dioxide is combined with colloidal silver homogeneously dispersed in solvent using a binder, instead of using the complicate processes of mixing, hydrothermal synthesis of a complex, intermetallic substitution, and sintering. The present invention is the result of overcoming such problems with the prior art.

In addition to the simplicity of synthesis, the present invention enjoys the combined effect sterilizing activity against bacteria, fungi and viruses of both silver and titanium dioxide. The inorganic solution comprising colloidal silver and titanium dioxide particles maintains potently antibacterial, antifungal and antiviral activity in the presence or absence of light.

The solution according to the present invention is effective for inhibiting a broad spectrum of viruses, bacteria and fungi and removing stingy odors. Particularly, the composition of the present invention has potently sterilizing activity against SARS coronavirus (TGEV, PEDV), avian influenza (AI) virus, swine influenza (SI) virus, human influenza (HI) virus, hand, foot and mouth disease virus, and new super bacteria (NDB-1) at a killing rate of 99.9% or higher.

Further, the composition of the present invention is highly adhesive so that a material of interest can retain potently anti-bacterial, anti-fungal and anti-viral activity for a long period of time after being applied with the composition.

Moreover, the composition of the present invention can decompose formaldehyde and ammonia, which cause sick house syndrome.

SUMMARY OF THE INVENTION

It is therefore an object of the present invention to provide an anti-bacterial, anti-fungal and anti-viral composition with excellent sterilizing power, deodorization and adhesion activity.

It is another object of the present invention to provide a product to which the composition of the present invention is applied.

It is a further object of the present invention to provide a method for preparing the composition, comprising i) reacting a silver precursor with a first alcohol containing at least one dispersion stabilizer to produce a silver colloid solution; ii) adding a titanium precursor, a second alcohol and an acid catalyst to a dilution of the silver colloid solution in water to generate titanium dioxide nanoparticles in the silver colloid solution; and iii) adding a binder to the silver colloid solution containing the titanium dioxide nanoparticles for formulation.

It is understood to those skilled in the art from the following detailed description that the technical objects to be achieved are not limited to those given above.

In accordance with an aspect thereof, the present invention provides an anti-bacterial, anti-fungal and anti-viral composition, comprising colloidal silver in an amount of from 11 to 15 wt %, titanium dioxide in an amount of from 18 to 25 wt %, a dispersion stabilizer in an amount of from 0.01 to 10 wt %, a binder in an amount of from 0.1 to 4 wt %, and a balance of water in an amount required to form 100 wt %.

In accordance with another aspect thereof, the present invention provides an application coated with the anti-bacterial, anti-fungal and anti-viral composition comprising colloidal silver in an amount of from 11 to 15 wt %, titanium dioxide in an amount of from 18 to 25 wt %, a dispersion stabilizer in an amount of from 0.01 to 10 wt %, a binder in an amount of from 0.1 to 4 wt %, and a balance of water in an amount required to form 100 wt %.

In one embodiment, the application may be selected from among a filter, a mask, carpet, clothing, and bedding, all of which are adapted for sanitizing bacteria, viruses and fungi.

In accordance with a further aspect thereof, the present invention provides a method for preparing an anti-bacterial, anti-fungal and anti-viral composition, comprising i) reacting 15~25 wt % of a silver precursor with 30~50 wt % of a first alcohol in the presence of 0.1~10 wt % of at least one dispersion stabilizer in a balance of water in an amount required to form 100 wt % to produce a silver colloid solution; ii) adding 15~20 wt % of a titanium precursor, 10~30 wt % of a second alcohol and 0.1~10 wt % of an acid catalyst to a dilution of 10~14 wt % of the silver colloid solution in a balance of water in an amount required to form 100 wt % to generate titanium dioxide nanoparticles in the silver colloid solution; and iii) adding 0.90~26.6 wt parts of a binder to 100 wt parts of the silver colloid solution containing the titanium dioxide nanoparticles for formulation.

In one embodiment, the silver precursor of step i) may be silver nitrate ($AgNO_3$) or silver acetate ($CH_3COOAg$).

In another embodiment, the alcohols used in steps i) and ii) may be independently selected from the group consisting of methanol, ethanol, isopropanol and butanol.

In another embodiment, the dispersion stabilizer of step i) may be selected from the group consisting of lysolecithin, flavonoid, Tween 20, Tween 40, Tween 80, polyvinylpyrrolidone, polyvinylalcohol, and a combination thereof.

In another embodiment, the titanium precursor of step ii) may be selected from the group consisting of TTIP (titaniumtetraisopropoxide), TEOT (titaniumethoxyorthotitanate), TBOT (titaniumbutoxyorthotitanate), and a combination thereof.

In another embodiment, the acid catalyst of step ii) may be selected from the group consisting of nitric acid, chloric acid, sulfuric acid and oxalic acid.

In another embodiment, the binder of step iii) may be selected from the group consisting of acryls, urethanes, and epoxides.

In another embodiment, the silver precursor of step i) is reacted at a temperature of from 65 to 95° C. for a time period of 2 to 6 hours.

In another embodiment, the titanium precursor of step ii) is reacted at a temperature of from 55 to 90° C. for a time period of 3 to 9 hours.

In another embodiment, the colloidal silver and the titanium dioxide particles independently range in size from 1 to 100 nm.

DESCRIPTION OF THE PREFERRED EMBODIMENTS

In accordance with an aspect thereof, the present invention contemplates a method for preparing an anti-bacterial, anti-fungal and anti-viral composition. First, a first alcohol containing at least one dispersion stabilizer is reacted with a silver precursor to give a silver colloid solution. In this regard, the silver colloid solution is made of 15 wt %~25 wt % of the silver precursor, 30 wt %~50 wt % of the first alcohol, 0.1 wt %~10 wt % of the dispersion stabilizer, and a balance of water in an amount required to form 100 wt %.

Preferably, the colloidal silver particles range in average diameter from 1 nm to 100 nm. Approximately 25 wt % silver colloid solution is obtained. Preferably, this silver colloid solution is diluted to a concentration of 11~15 wt % in water.

The silver precursor is preferably silver nitrate ($AgNO_3$) or silver acetate ($CH_3COOAg$).

In preferred embodiments, the first alcohol is selected from the group consisting of methanol, ethanol, isopropanol and butanol while the dispersion stabilizer is selected from the group consisting of lysolecithin, flavonoid, Tween 20, Tween 40, Tween 80, polyvinylpyrrolidone, polyvinylalcohol and a combination thereof.

Further, the silver precursor is reacted at a temperature of 65~95° C. for 2~6 hours.

Next, a titanium precursor, a second alcohol and an acid catalyst are added to a dilution of the silver colloid solution in water to form titanium dioxide nanoparticles in the silver colloid solution. In this regard, the silver colloid nanoparticles are used in an amount of from 10 wt % to 14 wt %, the titanium precursor in an amount of from 15 wt % to 20 wt %, the second alcohol in an amount of from 10 wt % to 30 wt %, the acid catalyst in an amount of from 0.1 wt % to 10 wt %, and a balance of water in an amount required to form 100 wt %.

Preferably, the titanium precursor is selected from the group consisting of TTIP (titanium tetraisopropoxide), TEOT (titanium ethoxyorthotitanate) and TBOT (titanium butoxyorthotitanate).

In some preferred embodiments, the second alcohol is selected from the group consisting of isopropanol, ethanol and butanol and the acid catalyst is selected from the group consisting of nitric acid, chloric acid, sulfuric acid and oxalic acid.

Further, the titanium precursor is preferably reacted at a temperature of 55~90° C. for 3~9 hours to form titanium dioxide nanoparticles with a size of 1 nm~100 nm.

The resulting silver colloid solution contains 1~5 wt % of titanium dioxide particles having an average diameter of 1~100 nm. When titanium dioxide is formed in a silver colloid solution, if the concentration of silver colloid is higher than a critical value or if the concentration of titanium dioxide used in a sol-gel reaction is high, the stability of silver colloid-titanium dioxide becomes poor, thus causing precipitation.

According to the method of the present invention, the use of the silver colloid nanoparticles at a concentration of 11~15 wt % and the titanium dioxide at a concentration of 18~25 wt % guarantees the homogeneous dispersion of the nanoparticles without aggregation.

The composition prepared according to the method of the present invention may be preferably neutralized with a base before use.

A high concentration of the nanoparticles in the solution causes the particles to aggregate together by self-assembly, so that the particles become large in size and precipitate, thus making it difficult to maintain homogeneity. In order to overcome this problem, colloidal silver nanoparticles are formed, followed by the synthesis of titanium dioxide nanoparticles through hydrolysis and condensation in accordance with the present invention.

Finally, a binder is added to the silver colloid solution containing the titanium dioxide nanoparticles. The binder is used in an amount of from 0.90 to 26.6 wt parts based on 100 wt parts of the silver colloid solution.

The binder may be selected from the group consisting of acryls, urethanes and epoxides.

The anti-bacterial, anti-fungal and anti-viral composition prepared according to the method of the present invention comprises colloidal silver in an amount of from 11 to 15 wt %, titanium dioxide in an amount of from 18 to 25 wt %, the dispersion stabilizer in an amount of from 0.01 to 10 wt %, and the binder in an amount of from 0.1 to 4 wt %, and a balance of water in an amount required to form 100 wt %.

If colloidal silver is used in an amount less than 11 wt %, the composition has poor antibacterial activity. On the other hand, if the amount of the colloidal silver exceeds 15 wt %, excessive precipitates are formed. Herein, the size of the silver colloid particles is on the order of 1 nm~100 nm.

A concentration of the titanium dioxide less than 18 wt % decreases the deodorizing activity. A concentration higher than 25 wt % causes the formation of excessive precipitates. Herein, the titanium dioxide nanoparticles range in size from 1 to 100 nm.

When the concentration of the dispersion stabilizer is less than 0.01 wt %, the nanoparticles are weakly dispersed. A concentration exceeding 10 wt % is extravagant.

If the binder is used at a concentration less than 0.1 wt %, the composition has weak adhesive force. On the other hand, a concentration over 4 wt % inhibits the dispersion of the particles to form precipitates.

The anti-microbial mechanism of the composition prepared according to the method of the present invention may be explained largely in two different ways. First, the composition interferes with an absorption system (e.g., Coenzyme A) necessary for oxidative and digestive metabolism in viruses, bacteria and fungi (e.g., by binding nanoparticles to viruses to cause aggregation) to asphyxiate or starve the microbes. That is, the nanoparticles bind to proteins such as transmembrane proteins and enzymes to inhibit the energy metabolism of the microbes. Next, the nanoparticles penetrate into microbes such as viruses and bacteria to destroy intracellular structures. Nanoparticles form strong and instant bonds with —SH, —COOH, and —OH groups of microbes to rupture the cell membranes and disturb the cells.

As described above, the composition prepared according to the method of the present invention may be diluted in distilled water or alcohol before being sprayed, may be formulated into sprayable forms, vials, sprays or aerosols, or may be impregnated into natural fibers, non-woven fabrics, masks, filters, etc. to produce anti-microbial and sanitizing products.

Also, there may be applications coated with the composition of the present invention. Among them are filters for killing bacteria, viruses and fungi (filters for air conditioners in automobiles, houses, and industries), carpets, masks and bedding. So long as it can be coated with the composition of the present invention, any application is within the scope of the present invention.

As will be elucidated in the following Example section, the composition of the present invention can effectively kill the new influenza A virus (H1N1).

Thus, infection by the new influenza can be prevented by applying the anti-bacterial, anti-fungal and anti-viral composition to necessary places.

The composition prepared according to the method of the present invention was assayed for its sterilizing activity against *Staphylococcus aureus, Escherichia coli*, new super bacteria (NDM-1), fungi, viruses including SARS coronaviruses, enterovirus type 71, and human influenza virus, for the duration of sanitizing effects, for its deodorization activity against ammonia and formaldehyde, for oral toxicity, and for dermal safety. Details of each test are as follows.

A. Antibacterial Activity Against *Staphylococcus aureus*

1. The test strain was incubated overnight at 37° C. in 5 mL of LB broth (peptone 10 g, yeast extract 5 g, NaCl 10 g, agar 15-20 g/L).

2. The cells were grown to an O.D. (optical density) of 0.5 at 660 nm

3. The test strain grown to an $OD_{600}$ of 0.5 was 100-fold diluted in 5 mL of LB broth.

4. Sample treatment

Concentration: The concentrations of samples were $10^3$ fold diluted.

Incubation time: The samples were cultured for one or three hours before dilution (100 and 10,000 folds) and 100 μL of each of the samples was spread on an LB plate (LB broth+agar 15~20 g/L) and incubated overnight at 37° C.

5. Colonies were counted, followed by comparison of the counts between sample-treated or non-treated groups to determine antibacterial activity.

B. Antibacterial Activity Against *Escherichia coli*

After *E. coli* was spread over plates, a $10^3$-fold dilution of the compound of the present invention in distilled water was sprayed three times (ca. 0.5 mL) over the plates. The plates were incubated for 24 hours in an incubator equipped with three fluorescent lamps. Colonies were counted to determine antibacterial activity.

C. Antibacterial Activity Against New Super Bacteria NDM-1

In MicroBioTest (MBT), Inc., a test authority approved as a GLP (Good Laboratory practice) by the FDA, a bactericidal efficacy test was performed on the new super bacteria NDM-1.

D. Antifungal Activity Against Five Strains

The assay of the composition of the present invention for antifungal activity was performed on five fungal strains (*Aspergillus niger* ATCC 9642, *Chaetomium globosum* ATCC 6205, *Penicillium pinophilum* ATCC 11787, *Gliocladium virens* ATCC 9645, *Aureobasidium pullulans* ATCC 15233) according to ASTM G 21-96 (2002). The test temperature and period are as follows.

1. Test Temp.: 28±1° C.
2. Test Period of time: 4 weeks

E. Antiviral Activity Against Coronaviruses

PEDV (Porcine Epidemic Diarrhea Virus) and TGEV (Transmissible GastroEnteric Virus), which are coronaviruses, were selected as test strains. PEDV can proliferate in a Vero cell line, which is a monkey kidney cell line. Vero E6 cells are derived from Vero cells, with almost identical properties there between. The test method, sample treatment and assay are as follows.

1. The virus host cell line Vero was plated at a density of $2 \times 10^4$ cells/well onto 96-well plates and incubated for 16 hours to form a monolayer of cells on the bottom of each well.

2. The composition of the present invention was 10-fold serially diluted in distilled water and added to a viral solution with a certain concentration. After incubation at 4° C. for 30 min, the mixture was inoculated into each well of the plates on which the cells were cultured.

3. As controls, a cell culture devoid of the composition of the present invention, a cell culture containing the virus alone, and a cell culture containing the composition of the present invention were all used, so that no viruses were used.

4. The incubation of the 96-well plates was stopped 40 hours after inoculation, and the cells were fixed with a 70% acetone solution and completely dried.

5. Proteins existing on each well were stained with SRB (0.4% Sulforhodamine B in 1% acetic acid) and dissolved again before measuring absorbance on an EIA reader (96 well plate reader). Absorbance values from groups treated with and without the composition of the present invention were analyzed.

6. Each experiment was conducted in triplicate.

7. Absorbance values of a group treated without the virus (A), with the composition of the present invention (B), with the virus alone (C) and with both the virus and the composition of the present invention (D) were calculated according to the following equation to evaluate the antiviral activity of the composition of the present invention.

$$\text{Antiviral Activity}(\%) = (D-C)/(B-C) \times 100$$

F. Antiviral Activity Against Influenza Viruses
1. Human Influenza (HI) virus
In vitro assay for antiviral activity
Condition: contact for one hour
Method: Plaque assay: pfu (plaque forming unit) was calculated using MDCK cells
  1) Influenza A virus (H3N2)
  Test virus: A/Shangdong/9/93 EC50: 0.02-0.04%
  2) Influenza A virus (H1N1)
  Test virus: A/Bayern/7/95 $EC_{50}$: 0.08-0.16%
  A/PR/8/34 $EC_{50}$: 0.04-0.08%
  3) Influenza B virus
  Test virus: B/Yamagata/16/88 $EC_{50}$: 0.02-0.04%
  4) Time taken to inactivate 50%: within 1~5 min after contact with 1% solution, within one hour after contact with 0.05% solution
2. Avian influenza (AI) virus
In vivo assay for antiviral activity
Condition: contact for one hour
Method: Proliferation of virus in fertilized eggs (infectious index $EC_{50}$ in fertilized eggs calculated)
Test virus: avian influenza virus subtype H9N2 $EC_{50}$: 0.02-0.04%

G. Activity of Inactivating New Flu Virus H1N1
1. Assay for the ability of the composition of the present invention to inactivate new flu virus
  1) The compound of the present invention is diluted 10-fold in PBS (pH 7.4).
  2) 100 μL of the new flu virus (H1N1) with $10^6$ $EID_{50}$/ml was applied to the diluted composition ($EID_{50}$=50% egg infective dose).
  3) The virus was incubated at room temperature for 20 min.
  4) The viral solution was 10-fold serially diluted in PBS.
  5) The serially diluted solutions were inoculated into fertilized eggs 10 days old.
  6) After incubation at 35° C. for 48 hours in a hatcher, the fertilized eggs were stored at 4° C. for 4 hours in a refrigerator.
  7) $Log_{10}EID_{50}$/ml was measured using a hemagglutination to determine the presence of viruses in the refrigerated, fertilized eggs
2. Measurement of the ability of filter coated with the composition of the present invention to inactivate new flu Virus
  1) Filters treated with or without the composition of the present invention are cut into a size of about 2 cm×2 cm and placed on Petri dishes.
  2) 100 mL of the new flu virus with $10^6$ $EID_{50}$/ml is applied to the filter fragments.
  3) The filter fragments treated with the virus are incubated at room temperature for 20 min.
  4) After incubation for 20 min, the filter fragments are washed with 1 mL of PBS (pH 7.4) and the PBS was 10-fold serially diluted.
  5) The PBS dilutions are inoculated into 10-day-old fertilized eggs.
  6) After being incubated at 35° C. for 48 hours in a hatcher, the fertilized eggs are refrigerated at 4° C. for 4 hours.
  7) $Log_{10}EID_{50}$/ml is measured using a hemagglutination to determine the presence of viruses in the refrigerated, fertilized eggs.

H. For measuring antiviral activity, a virucidal efficacy test was performed on against human Enterovirus type 71(EV 71) in MicroBioTest (MBT), Inc., a test authority approved as a GLP (Good Laboratory practice) by the FDA.

I. An adhesive test is performed in such a way that the antibacterial activity of textiles treated with the composition of the present invention is measured according to KS K 0693: 2006 after they are laundered 50 times under the conditions set forth in KS K ISO 6330:2006 8B, (40±3° C.). Mesh dry.

J. A test for deodorizing ammonia and formaldehyde is conducted according to KS I 2218:2009.

K. Safety from Oral Toxicity and Skin Irritation
Oral toxicity and skin irritation tests are conducted according to Notification No. 1999-61 of the Korean Food and Drug Administration.

Method for Synthesizing the Composition According to the Present Invention

Colloidal silver was synthesized using an alcohol reduction method. First, 20 g of silver nitrate ($AgNO_3$) was dispersed at 80° C. for 5 hours in 40 g of ethanol in the presence of 0.01 g of flavonoid, a dispersion stabilizer. The silver colloid solution thus prepared contained silver particles at a concentration of 25 wt %, with an average particle size of from 1 to 100 nm. This solution was diluted in water to a concentration of 11 to 15 wt %.

Subsequently, a mixture of 20 g of TEOT (titaniumethoxyorthotitanate) and ethanol was added to the silver colloid solution diluted to a concentration of 11 wt % and subjected to hydrolysis and condensation at room temperature using a sol-gel method.

In this regard, 5 g of nitric acid ($HNO_3$) was used as a catalyst for hydrolysis. The reaction was carried out at a temperature of 60~85° C. for 4~8 hours, with stirring, so that milk white titanium dioxide particles with an average size of 1~100 nm were formed at a concentration of 18~25 wt %.

Finally, 0.1 g of a binder was added to the silver colloid solution containing titanium dioxide particles to afford the composition of the present invention.

Compositions according to the present invention were prepared in the same manner with the exception that silver nitrate, TEOT and a binder were used in the amounts given in Table 1, below.

TABLE 1

|  | Silver Nitrate content (g) | Ethanol content (g) | Flavonoid content (g) | TEOT content (g) | Nitric acid content (g) | Binder content (g) | Stability |
|---|---|---|---|---|---|---|---|
| Ex. 1 | 20 | 40 | 0.01 | 20 | 0.5 | 0.1 | ○ |
| Ex. 2 | 25 | 40 | 0.01 | 20 | 0.5 | 0.1 | ○ |
| Ex. 3 | 25 | 40 | 0.01 | 20 | 0.5 | 0.1 | ○ |
| Ex. 4 | 30 | 40 | 0.01 | 20 | 0.5 | 0.1 | X |
| Ex. 5 | 20 | 40 | 0.01 | 10 | 0.5 | 0.1 | ○ |
| Ex. 6 | 20 | 40 | 0.01 | 20 | 0.5 | 0.1 | ○ |
| Ex. 7 | 20 | 40 | 0.01 | 40 | 0.5 | 0.1 | X |
| Ex. 8 | 20 | 40 | 0.01 | 20 | 0.5 | 0.05 | X |
| Ex. 9 | 20 | 40 | 0.01 | 20 | 0.5 | 5 | X |

○: no precipitations, colloids of stable silver-titanium dioxide synthesized
X: precipitation just after synthesis A. Results of Antibacterial Test Against *Staphylococcus aureus*

The antibacterial activity of the composition of the present invention was compared to that of the composition prepared according to a conventional mixing method. When the compositions were applied for 1 hour, they removed *Staphylococcus aureus* at a rate of 100% and 63%, respectively. The test results are summarized in Table 2, below.

TABLE 2

Comparison of Antibacterial Activity of Compositions against *Staphylococcus aureus* (cfu/plate)

|  | Inventive Ag Colloid/ TiO$_2$ Solution 1/100 Diluted at O.D. = 0.5 | | Solution Prepared by Conventional Mixing Method 1/100 Diluted at O.D. = 0.5 | |
|---|---|---|---|---|
| *Staphylococcus aureus* | 1 hour $10^{-4}$-fold dilution | 3 hours $10^{-4}$-fold dilution | 1 hour $10^{-4}$-fold dilution | 3 hours $10^{-4}$-fold dilution |
| Control No. of Surviving Cells/Removal Rate (%) | ~1,000 0/100 | Innumerable 0/100 | 582 216/63 | Innumerable 280/— |

*: the conventional method is a simple mixing method in which colloidal silver and titanium dioxide solutions are separately prepared and simply mixed together at a ratio of 8:2.

B. Results of Antibacterial Test Against *E. coli*

The composition of the present invention removed *E. coli* at a rate of as high as 99.999%.

C. Results of Antibacterial Test Against New Super Bacteria (NDM-1)

The composition of the present invention exhibited excellent antibacterial activity, removing super bacteria at a rate of as high as 99.999%.

TABLE 3

Initial Count and Test Results Expressed as Average CFU per mL Recovered, Percent and Log$_{10}$ Reduction NDM-1 Producing *Klebsiella pneumoniae*, Cl 10002

| Initial Count (CFU/mL) Sample time point | Rep | Test Recovered (CFU/mL) | Percent reduction | Log$_{10}$ reduction |
|---|---|---|---|---|
| 3.0 × 10$^6$ | 1 | <5.0 × 10$^0$ | >99.999 | 5.76 |
| (Immediate sample) | 2 | <5.0 × 10$^0$ | >99.999 | 5.78 |
| 2.8 × 10$^6$ | 1 | <5.0 × 10$^0$ | >99.999 | 5.75 |
| (40 minutes) | 2 | <5.0 × 10$^0$ | >99.999 | 5.75 |

D. Results of Antifungal Activity Against Five Fungal Strains

The composition of the present invention was classified as grade "0", which indicates the allowance of no growth of five fungal strains, as shown in Table 4, below.

TABLE 4

| Strain | *Aspergillus neger* ATCC 9642 *Chaetomium globosum* ATCC 6205 *Penicillium pinophilum* ATCC 9645 *Aureobasidium pullulans* ATCC 15233 | ASTM G 21- 96(2002) |
|---|---|---|
| Grade | 0 | |

E. Results of Antiviral Test Against Corona Viruses

An antiviral test was performed in triplicate, and similar results were obtained. No cytotoxicity was found in the composition of the present invention when it was diluted as mentioned above. However, a 100-fold dilution of the composition showed antiviral activity against PEDV (Porcine Epidemic Diarrhea Virus) and TGEV (Transmissible Gastroenteric Virus) at a rate of 99.99% or higher. Even when it was 1.000-fold diluted, the composition inhibited the growth of the viruses at a rate of 99.9% and 93.0%, respectively. As a rule, the antiviral activity of the composition increased with concentration.

TABLE 5

| Test Method Activation | Composition of the Invention | | | |
|---|---|---|---|---|
|  | Efficiency(100-fold dilution) | | Efficiency (1,000-fold dilution) | |
| Test | PEDV | TGEV | PEDV | TGEV |
| Antiviral Activity | ≥99.99% | ≥99.9% | ≥99.9% | ≥93.0% |

F. Results of Antiviral Test Against Influenza Viruses

The composition of the present invention was verified to have sterilizing activity against human influenza virus and avian influenza virus as measured by a test method for antiviral activity.

TABLE 6

| Type | Human Influenza virus; Type: H1N1, type A: H3N2, type B | Avian Influenza Virus; H9N2 |
|---|---|---|
| Result | EC$_{50}$: 0.02~0.04% | EC$_{50}$: 0.02~0.04% |

G. Test for Ability to Inactivate New Flu Virus (H1N1)

The composition of the present invention was assayed for ability to inactivate new flu virus according to a test protocol, and it was found that it removes the new flu virus at a rate of 100%. In addition, the removal rate of the filter treated with the composition was measured to be 99.99% for the new flu virus.

TABLE 7

| Sample | Viral Titer (log$_{10}$EID$_{50}$/ml) | | | | |
|---|---|---|---|---|---|
| Inventive composition | 0 | 0 | 0 | 0 | 0 |
| Filter treated with the inventive composition | <1.0 | <1.0 | <1.0 | <1.0 | <1.0 |
| Filter treated without the inventive composition | 6.0 | 6.5 | 6.5 | 6.0 | 6.0 |
| Viral control | 6.5 | 6.0 | 6.5 | 6.5 | 6.0 |

H. Test of Antiviral Activity Against Hand, Foot and Mouth Disease Virus

After it was in contact with the hand, food and mouth disease virus for 20 min, the composition of the present invention inhibited the growth of the virus at a rate of 99.8% or higher.

TABLE 8

| Test Agent | Contact Time | Initial Viral Load (Log$_{10}$TCID$_{50}$) | Output Viral Load (Log$_{10}$TCID$_{50}$) | Log$_{10}$ Reduction | Reduction (%) |
|---|---|---|---|---|---|
| G-SOL ® | 20 minutes | 5.53 ± 0.37 | 2.78 ± 0.28 | 2.75 ± 0.46 | 99.8222 |

I. Test for Deodorizing Activity of Removing Ammonia and Formaldehyde.

The composition of the present invention was found to remove ammonia at a rate of 100% and formaldehyde at a rate of 93.8%. The test results are summarized in Tables 9 and 10, respectively.

TABLE 9

| Item | Passed Time(min) | Conc. Of Blank(ppm) | Conc. Of Test Sample(ppm) | Rate of Deodorization(%) |
|---|---|---|---|---|
| Test of | 0 | 50 | 50 | — |
| Deodorizaton | 30 | 50 | 2 | 98.0 |
| (Ammonia, | 60 | 49 | 0 | 100.0 |
| $NH_3$) | 90 | 49 | 0 | 100.0 |
|  | 90 | 49 | 0 | 100.0 |
|  | 120 | 48 | 0 | 100.0 |
| Test Method | | KS I 2218:2009 | | |

TABLE 10

| Item | Passed Time(min) | Conc. Of Blank(ppm) | Conc. Of Test Sample(ppm) | Rate of Deodorization(%) |
|---|---|---|---|---|
| Test of | 0 | 50 | 50 | — |
| Deodorizaton | 30 | 50 | 10 | 80.0 |
| (Formaldehyde, | 60 | 49 | 6 | 87.8 |
| HCHO) | 90 | 49 | 0 | 100.0 |
|  | 90 | 49 | 4 | 91.8 |
|  | 120 | 48 | 3 | 93.8 |
| Test Method | | KS I 2218:2009 | | |

J. Test for Adhesion Activity

After being laundered 50 times, the textiles treated with the composition of the present invention were tested for antibacterial activity against *S. aureus* and *Pneumococcus*. Its antibacterial activity was measured to be 99.3% and 99.9% against the two strains, respectively, indicating the excellent adhesive potential of the composition.

TABLE 11

| TEST CONDUCTED | | TEST RESULT | |
|---|---|---|---|
| (01) ANTIBACTERIAL ACTIVITY OF TEXTILES (KS K 0693-2006): CFU. BACTERIOSTATIC REDUCTION RATE % | | | |
| | | BLANK | #1 |
| BACTERIA-1: | AT BEGINNING | $2.4 \times 10^4$ | $2.4 \times 10^4$ |
|  | AFTER 18 HRS. | $1.3 \times 10^6$ | $9.6 \times 10^3$ |
|  | BACTERIOSTATIC REDUCTION RATE | — | 99.3 |
| BACTERIA-2: | AT BEGINNING | $2.2 \times 10^4$ | $2.2 \times 10^4$ |
|  | AFTER 10 HRS. | $2.1 \times 10^7$ | $2.0 \times 10^3$ |
|  | BACTERIOSTATIC REDUCTION RATE | — | 99.9 |

NOTE)
STANDARD FEBRIC: COTTON
TEST BACTERIA: BACTERIA-1—*Staphylococcus aureus* ATCC 6538
BACTERIA-2—*Klebsiella pneumoniae* ATCC 4352.
< = LESS THAN
WASH CONDITION: KS K ISO 6330:2006. 88.
(40 ± 3) ° C. FLAT DAY. 50 CYCLE
SEE ATTACHED PHOTOS.

K. Safety Test

The composition of the present invention was subjected to an oral toxicity test and skin irritation test according to Notification No. 1999-61 of the Korean Food and Drug Administration, and the results are summarized in Table 12, below.

TABLE 12

| Test | Test Result | Method |
|---|---|---|
| Oral toxicity | The composition was orally administered only one time at a dose of 5,000 mg/kg B.W to rats. For 14 days, deaths of animals, clinical signs, body weights, and necropsy findings were observed. No clinical signs and lesions regardless of the treated dose were observed. There were no dead animals nor significant changes of body weight. Thus, the LD50 value of the composition was considered to be higher than 5,000 mg/kg B.W. in both male and female rats. | Notification No. 1999-61 of the KFDA |
| Skin irritation | Upon application thereof to the skin of New Zealand White rabbits, the composition did not cause erythema, callus and edema. Thus, its P.I.I. (Primary Irritation Index) was scored as "0.0", so that it was evaluated as being non-irritant on the skin. These results indicate that the composition can be applied to the body and animals without causing toxicity. | |

The antibacterial, antifungal and antiviral composition, the applications thereof and the preparation methods thereof in accordance with the present invention are not limited to those illustrated in the Examples. The Examples may be reconstituted to have various modifications from combinations of entirety or a part of the examples.

As illustrated above, the composition of the present invention exhibits potently sterilizing activity against bacteria, fungi and viruses.

Having high adhesion activity due to the binder, the composition of the present invention imparts excellent antibacterial activity to a product coated therewith for a long period of time.

Further, the composition of the present invention shows deodorization activity depending on the amount of the titanium dioxide nanoparticles.

Moreover, the composition of the present invention exhibits the synergistic effect of silver and photocatalyst nanoparticles, thus performing sterilizing activity against bacteria and viruses irrespective of the presence or absence of light and degradation activity for volatile organic compounds and stingy materials. In addition, the composition may be formulated into a sprayable form convenient for use.

Therefore, the composition of the present invention finds applications in various fields, including the sanitary field such as in potently inhibiting a broad spectrum of pathogenic microorganisms including SARS coronavirus, porcine epidemic diarrhea virus (PEDV), transmissible gastroenteritis virus, TGEV), human enterovirus type 71, human Influenza viruses, superbacteria, and fungi, and the environment field such as in achieving deodorization by degrading stingy materials and trace volatile organic compounds through oxidation.

Particularly, having excellent killing activity against infectious influenza viruses, the composition of the present invention is used in the prevention of diseases caused by infections influenza viruses. For example, a mask coated with the composition of the present invention is effective at preventing the spread of infectious influenza viruses.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for preparing a composition showing sterilizing activity against bacteria, fungi and viruses, comprising
   i) reacting 15~25 wt % of a silver precursor with 30~50 wt % of a first alcohol in the presence of 0.1~10 wt % of at least one dispersion stabilizer in a balance of water in an amount of 100 wt % to produce a silver colloid solution;
   ii) adding 15~20 wt % of a titanium precursor, 10~30 wt % of a second alcohol and 0.1~10 wt % of an acid catalyst to a dilution of 10~14 wt % of the silver colloid solution in a balance of water in an amount to 100 wt % of water to generate titanium dioxide nanoparticles in the silver colloid solution; and
   iii) adding 0.90~26.6 wt parts of a binder to 100 wt parts of the silver colloid solution containing the titanium dioxide nanoparticles to form a combination particle,
   wherein the combination particle consists of a silver colloid bound to a titanium dioxide nanoparticle by a binder selected from the group consisting of acryls, urethanes, and epoxides.

2. The method of claim 1, wherein the silver precursor of step i) is silver nitrate ($AgNO_3$) or silver acetate ($CH_3COOAg$).

3. The method of claim 1, wherein the alcohols used in steps i) and ii) are independently selected from the group consisting of methanol, ethanol, isopropanol and butanol.

4. The method of claim 1, wherein the dispersion stabilizer of step i) is selected from the group consisting of lysolecithin, flavonoid, Tween 20, Tween 40, Tween 80, polyvinylpyrrolidone, polyvinylalcohol, and a combination thereof.

5. The method of claim 1, wherein the titanium precursor of step ii) is selected from the group consisting of TTIP (titaniumtetraisopropoxide), TEOT (titaniumethoxyorthotitanate), TBOT (titaniumbutoxyorthotitanate), and a combination thereof.

6. The method of claim 1, wherein the acid catalyst of step ii) is selected from the group consisting of nitric acid, chloric acid, sulfuric acid and oxalic acid.

7. The method of claim 1, wherein the reaction of step i) is conducted at a temperature of 65~95° C. for 2~6 hours.

8. The method of claim 1, wherein the reaction of step ii) is conducted at a temperature of 55~80° C. for 3~9 hours.

9. The method of claim 1, wherein the colloidal silver particles and the titanium dioxide nanoparticles range in size from 1 nm to 100 nm.

* * * * *